United States Patent [19]

Malana

[11] Patent Number: 4,797,125
[45] Date of Patent: Jan. 10, 1989

[54] ELECTRODE CONNECTOR FOR SUBSTRATE ELECTRODES

[75] Inventor: Anthony Malana, San Dimas, Calif.
[73] Assignee: Tronomed, Inc., Laguna Hills, Calif.
[21] Appl. No.: 55,163
[22] Filed: May 27, 1987
[51] Int. Cl.⁴ .............................................. H01R 4/48
[52] U.S. Cl. .................................. 439/729; 128/639; 439/838
[58] Field of Search ........ 439/506, 729, 731, 835–838; 128/639, 640, 798, 802

[56] References Cited

U.S. PATENT DOCUMENTS

| | | | |
|---|---|---|---|
| 3,606,881 | 9/1971 | Woodson | 128/206 E |
| 4,072,388 | 2/1978 | Dunn | 339/103 R |
| 4,555,155 | 11/1985 | Drake | 439/492 |
| 4,702,256 | 10/1987 | Robinson et al. | 439/729 |

Primary Examiner—Gil Weidenfeld
Assistant Examiner—Paula A. Austin
Attorney, Agent, or Firm—Price, Gess & Ubell

[57] ABSTRACT

A medical electrode connector for a flexible resting electrode is provided. A first base member has a receptacle while a second movable member has a plastic prong of a configuration compatible with movement into the receptacle. A flexible electrode can be positioned between the receptacle and the prong and a spring can force the prong member to deform and cause an electrical connection with the flexible electrode.

19 Claims, 1 Drawing Sheet

ELECTRODE CONNECTOR FOR SUBSTRATE ELECTRODES

BACKGROUND OF THE INVENTION

1. Field of the Invention

The present invention is directed to an electrode connector for electrically engaging a flexible resting electrode such as an electrocardiographic electrode and more particularly to an improved electrode connector to provide a secure attachment to a flexible electrode.

2. Description of Related Art

The medical industry has used a large number of electrical and electrode connectors for attachment to substrate electrodes on patients. This field is relatively crowded and designs are usually controlled by, first, a requirement for a secure fastening of an electrode connector to an electrode since it can be part of a life support system and second, by the economics of providing relatively easily disposable and replaceable electrode connectors to maintain sterility in a medical environment.

An example of a flexible electrode and a electrode clip can be seen in U.S. Pat. No. 3,606,881. An alternative embodiment of an electrode lead clip can be seen in U.S. Pat. No. 4,072,388. Finally, another electrical connector can be seen in U.S. Pat. No. 4,206,960 that comprises a pair of electrode receptacles with a sliding fastener for locking the electrical connector to a terminal stud.

Recently the medical field has utilized flexible electrodes that incorporated a portion of the flexible electrode member as the contact area of the electrode. The medical field has utilized a variation of the standard electrical alligator clip, which in essence is an industrial alligator clip with a heat-shrunk plastic sheath extending over a majority of the portion of the clip member. The open jaw portion of the alligator clip simply grasps the contact portion of the electrode. Another electrode lead wire set has used an electrical connector having a conventional alligator clip form with a combination of side-serrated teeth and opposed rows of parallel teeth. Again, the electrode connector simply grasps the exposed contact edge of the flexible electrode.

Patients usually have the flexible electrode attached directly to their skin for extended periods of time and frequently voluntary or involuntary moves cause dislocating forces between the electrode connector and the flexible electrode contact portion.

There is a present demand in the medical field to provide a relatively permanent connection of an electrical connector to a flexible electrode contact at a relatively low cost so that it can be easily disposed. Since the problems of dislodging the connection of an electrode connector member from an electrode on the patient's skin is a constant recurring problem, the prior art is still seeking to optimize a medical electrode connector that will resolve these issues.

SUMMARY OF THE INVENTION

The present invention is directed to a medical electrode connector for substrate flexible electrodes and includes a first base member having a receptacle and a second member movably attached to the first member and having a prong member of a configuration compatible with movement into the receptacle. An electrical contact plate is provided on one of the receptacle and prong members for providing an electrical contact with the flexible electrode when the prong member is positioned on one side of the electrode and the receptacle is positioned on the other side. The prong member forces the electrode to be deformed and to be positioned within the receptacle to thereby provide a positive locking electrical contact.

A feature of the invention is to provide a secure relatively permanent connection to a throw-away flexible electrode that can be easily opened and connected to the flexible substrate electrode.

The objects and features of the present invention, which are believed to be novel, are set forth with particularity in the appended claims. The present invention, both as to its organization and manner of operation, together with further objects and advantages thereof, may best be understood by reference to the following description taken in connection with the accompanying drawings.

DESCRIPTION OF THE PREFERRED EMBODIMENT

The following description is provided to enable any person skilled in the medical field to make and use the invention and sets forth the best mode contemplated by the inventor of carrying out his invention. Various modifications, however, will remain readily apparent to those skilled in the art since the generic principles of the present invention have been defined herein specifically to provide a relatively economical, reliable and secure electrode connector that can be used with a flexible substrate electrode.

Figure 1:
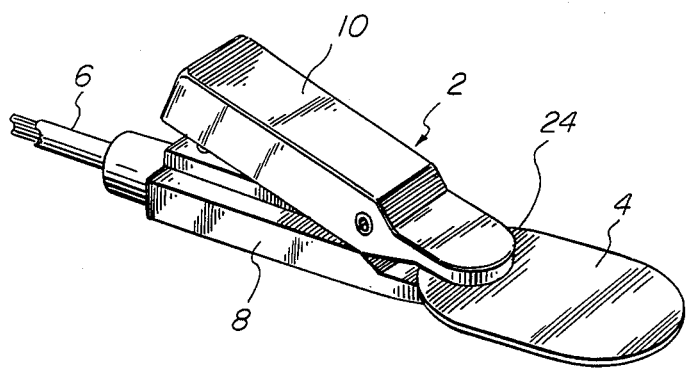
FIG. 1 is a side perspective view of a medical electrode connector of the present invention connected to a flexible substrate electrode.
Figure 2:
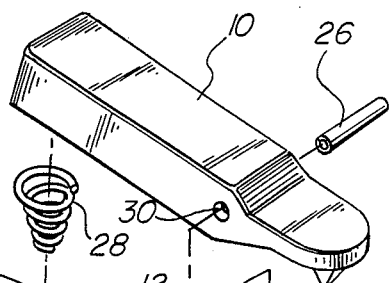
FIG. 2 is a partial exploded perspective view of the electrode connector of the present invention.
Figure 3:
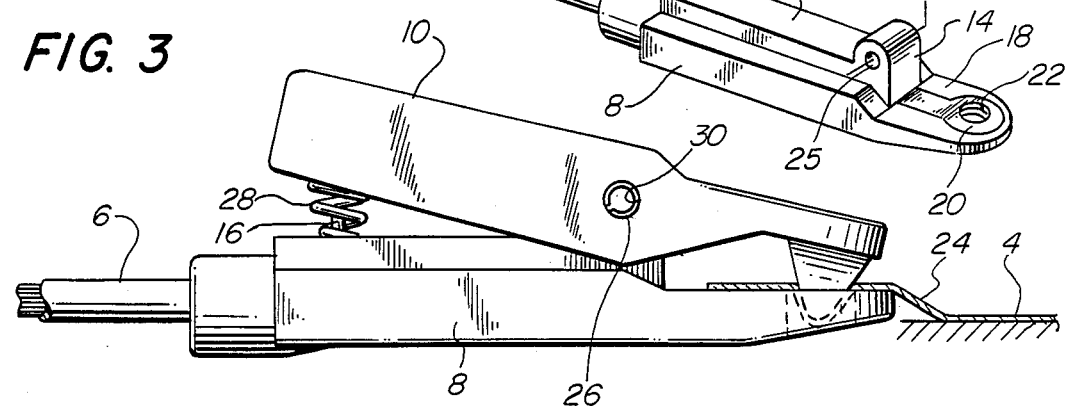
FIG. 3 is a side view of the invention.

Referring to FIGS. 1 and 2, a perspective view of the electrode connector 2 of the present invention is shown connected to a flexible substrate electrode 4. As can be appreciated, the electrode connector 2 is connected to an appropriate lead wire 6 and comprises a first base member 8 and a second movable member 10. Each of these members can be appropriately molded from a medical grade plastic. The lower base member 8 has a central support platform 12 which includes a mounting post 14 at one end and a supporting guide post 16 at the other end. Adjacent to mounting post 14 is a flat surface contact portion 18 that can support a ring-shaped electrode plate 20 positioned about an aperture or a receptacle 22. The electrode plate 20 provides the electrical contact with an exposed portion 24 of the flexible substrate electrode 4 as can be seen in FIG. 3. The electrode plate 20 is electrically connected to the lead wire 6 and can be mounted in an appropriate cavity during production with the plastic molded about the electrode plate 20.

The mounting post 14 has a bore 25 that extend traverse to the longitudinal axis of the base member 8. A pivoting shaft or sleeve 26 can extend through the bore 24 and can capture the movable member 10. The movable member 10 is only relatively movable to that of the base member 8 since the connector is operated for grasping with a composite movement against a biasing helical spring 28. The movable member 10 has a pair of complimentary apertures 30 on upstanding side flanges 36 and 38 that frictionally receive and maintain the sleeve 26.

Figure 4:
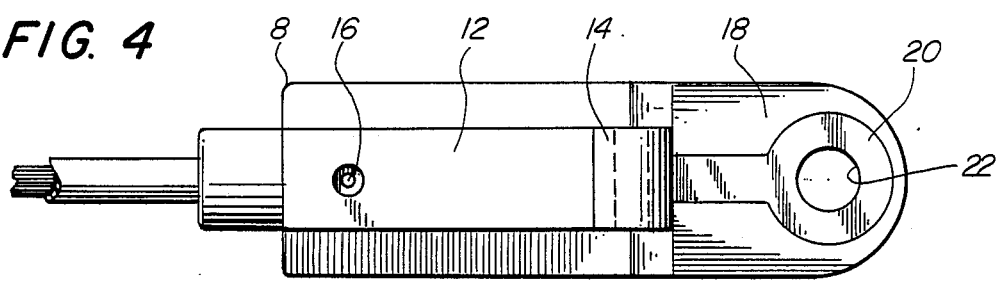
FIG. 4 is a plan view of one-half of the medical electrode connector.
Figure 5:
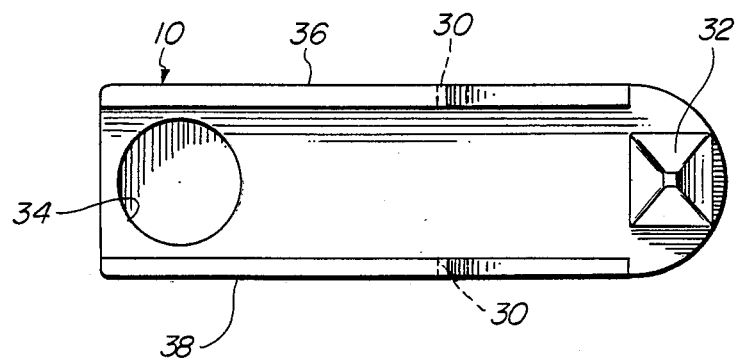
FIG. 5 is a plan view of the other half of the medical electrode connector.

The movable member 10 has at one end a prong 32 as seen in FIG. 5 that has a complimentary configuration that is capable of extending within the receptacle 22 shown in FIG. 4. In the disclosed embodiment, the plastic prong 32 has four side triangular facets that terminate in a point. However, other configurations are possible for the prong 32. At the other end of the movable member 10 is a recess 34 that is designed to capture the enlarged end of the helical spring 28 with the smaller portion of the spring coil designed to extend around the supporting post 16 on the base member. The side flanges 36 and 38 support the apertures 30 and are of such a configuration to extend around the platform 12 when the movable member 10 is operatively positioned and restrained by the sleeve member 26.

Alternatively, the base member's mounting post 14 can be molded with side cylindrical pins having a slanted surface (not shown) instead of the bore 25, and the side flanges 36 and 38 can have a complimentarily camming internal surface to permit a snap mounting of the base member 8 and the movable member 10 together. The side flanges being of such a thickness to permit sufficient flexing to capture the pins and the apertures 30.

As can be seen in FIG. 3, the contact portion 24 of the flexible electrode 4 is physically deformed by the prong 32 on the movable member 10 and is forced not only against the electrode plate 20 but also into the receptacle 22. The prong member 32 can actually penetrate or at least elastically deform a portion of the flexible substrate electrode 24 to provide a permanent affixation which can only be released by compression of the helical spring 28 or tearing of the substrate electrode 4. Thus, the electrode connector 2 of the present invention can be as permanently attached to the flexible substrate electrode 4 as the electrode 4 can be affixed to the surface of the patient's skin. Accordingly, the conventional problem of dislocation of the electrode connector and lead from a flexible substrate electrode has been eliminated while still permitting the substrate electrode to be relatively inexpensively manufactured, without any requirement of studs or posts provided on the substrate electrode, while still permitting a permanent attachment by an electrode connector. In the present invention, the stud or prong post is provided on the electrode connector and it deforms the flexible substrate electrode to ensure a positive and locking contact with the electrode plate 20 on the base member 8.

As can be appreicated, the prong 32 can be coated with a metallic coating as an alternative configuration to provide an electrical contact but the above described configuration is more economical and practical.

While the above embodiment has been disclosed as the best mode contemplated by the inventor, it should be realized that this example should not be interpreted as limiting because artisans skilled in the electrical medical field, once given the present teaching, can vary from this specific embodiment. Accordingly, the scope of the present invention is to be determined solely from the following claims.

What is claimed is:

1. A medical electrical connector for flexible resting electrodes applied to a patient, comprising:
    a first base member having a flat support surface with a receptacle extending into the flat support surface;
    a second member attached to the first member and relatively movable with the first member, the second member having a prong member of a configuration compatible with movement into the receptacle; and
    means, on one of the receptacle and prong member, for providing electrical contact with the electrode when the prong member is positioned on one side of the electrode and the receptacle is positioned on the other side, the prong member forcing the electrode to be deformed and to be positioned within the receptacle for providing a positive locking contact.

2. The medical electrical connector of claim 1 wherein an electrical contact plate is positioned about the receptacle.

3. The medical electrical connector of claim 1 wherein the prong member has four triangular facets that extend to a point.

4. The medical electrical connector of claim 1 wherein the first base member and the second member are made of electrically insulated material, thereby insulating the electrical contact from outside influences.

5. The medical electrical connector of claim 1 wherein the first base member has a mounting post with a bore and the second member has a pivoting shaft that extends into the mounting post bore.

6. The medical electrical connector of claim 5 further including a spring member wherein the first base member has, adjacent one end, a supporting post and the second member has a complimentarily supporting recession for retaining the spring member.

7. A medical electrode connector for flexible resting electrodes applied to a patient, comprising:
    a first base member having a flat support surface with a receptacle apertured;
    a second plastic member attached to the first member and relatively movable with the first member, the second member having a plastic prong member of a configuration and a position compatible with movement into the receptacle; and
    means, on the flat surface of the receptacle, for providing electrical contact with the electrode when the plastic prong member is positioned on one side of the electrode and the receptacle is positioned on the other side and the prong member forces the electrode to be deformed and to be positioned within the receptacle for providing a positive locking contact and an electrical contact.

8. The medical electrical connector of claim 7 wherein the first base member and the second member are made of electrically insulated material, thereby insulating the electrical contact from outside influences.

9. The medical electrode connector of claim 7 wherein the plastic prong member has a configuration which extends away from the remainder of the second member to terminate as a reduced dimensional point.

10. The medical electrical connector of claim 7 wherein an electrical contact plate is positioned about the receptacle.

11. The medical electrical connector of claim 10 wherein the plastic prong member has four triangular side facets that extend to a point.

12. The medical electrical connector of claim 7 wherein an electrical contact plate is positioned about the receptacle.

13. The medical electrical connector of claim 12 further including a helical spring member wherein the first base member has, adjacent one end, a supporting post and the second member has a complimentarily supporting recession for retaining the helical spring member.

14. A medical electrode connector for flexible resting electrodes applied to a patient, comprising:
- a first base member having a supporting surface with a receptacle extending into the supporting surface and spaced inward from an end of the base member;
- a second member attached to the first member and relatively movable with the first member, the second member having a prong member of a configuration and a position compatible with movement into the receptacle, and
- means, on the supporting surface of the first base member, for providing electrical contact with the electrode when the prong member is positioned on one side of the electrode and the receptacle is positioned on the other side and the prong member creates an indentation in the electrode, forcing the electrode to be positioned within the receptacle for providing a positive locking contact and an electrical contact.

15. The medical electrode connector of claim 14 wherein an electrical contact plate is positioned about the receptacle.

16. A two-piece plastic medical electrode connector for attachment to a flexible resting electrode applied to a patient, comprising:
- a first base member having adjacent one end an apertured receptacle spaced inward from the end of the base member;
- a second member attached to the first member and relatively movable with the first member, the second member having adjacent one end an integrally molded plastic prong member of a configuration and positioned compatible with movement into the apertured receptacle;
- means for biasing the prong member into the aperture receptacle, and
- means for providing electrical contact with the electrode when the prong member is positioned on one side of the electrode and the receptacle is positioned on the other side with the prong member forcing the electrode to be deformed and to be positioned within the receptacle for providing a positive locking contact.

17. The medical electrode connector of claim 16 wherein the means for providing electrical contact includes an annular electrode plate extending around the apertured receptacle when the prong member is biased into the apertured receptacle.

18. The medical electrical connector of claim 16 wherein the first base member has a mounting post with a bore and the second member has a pivoting shaft that extends into the mounting post bore.

19. The medical electrical connector of claim 16 wherein the means for biasing further includes a helical spring member wherein the first base member has, adjacent one end, a supporting post and the second member has a complimentarily supporting recession for retaining the helical spring member.

* * * * *